United States Patent [19]

Hauri

[11] 4,161,257
[45] Jul. 17, 1979

[54] CLOSURE FOR VACUUM BOTTLES AND THE LIKE

[75] Inventor: Hermann Hauri, Lenzburg, Switzerland

[73] Assignee: Genossenschaft Vebo Solothurnische Eingliederungs-Stätte für Behinderte, Zuchwil, Switzerland

[21] Appl. No.: 799,946

[22] Filed: May 24, 1977

[30] Foreign Application Priority Data

May 25, 1976 [CH] Switzerland ..................... 6758/76

[51] Int. Cl.² .......................................... B65D 51/16
[52] U.S. Cl. .................................. 215/260; 215/271; 215/262; 215/280; 215/100 A; 215/DIG. 3; 222/103
[58] Field of Search ............... 215/260, 262, 270, 271, 215/307, 309, DIG. 3, 280, 100 R, 100 A; 206/524.8; 128/276; 222/103

[56] References Cited

U.S. PATENT DOCUMENTS

| | | | |
|---|---|---|---|
| 1,094,192 | 4/1914 | Bean | 215/100 A |
| 1,694,851 | 12/1928 | Glass | 215/260 |
| 2,199,817 | 5/1940 | Flosdorf | 215/DIG. 3 |
| 2,334,905 | 11/1943 | Cherkin | 215/DIG. 3 |
| 2,744,631 | 5/1956 | Toombs | 215/100 R |
| 3,047,177 | 7/1962 | Poitras et al. | 215/260 |
| 3,151,757 | 10/1964 | Martin | 215/260 |
| 3,334,628 | 8/1967 | Saemann et al. | 128/276 |
| 3,814,098 | 6/1974 | Deaton | 128/276 |
| 3,949,744 | 4/1976 | Clarke | 222/103 |

FOREIGN PATENT DOCUMENTS

| | | | |
|---|---|---|---|
| 511935 | 6/1950 | Canada | 215/100 R |
| 172242 | 12/1921 | United Kingdom | 215/100 R |

*Primary Examiner*—William Price
*Assistant Examiner*—Joseph M. Moy
*Attorney, Agent, or Firm*—Peter K. Kontler

[57] ABSTRACT

The neck of a bottle is closed and sealed by a one-piece cap having a cylindrical portion which surrounds the neck, a deformable end wall which extends across the open end of the neck, and a flexible hose which is integral with the end wall. The inner side of the end wall has an annular bead which sealingly engages the inner surface of the neck when the pressure in the interior of the bottle is reduced below atmospheric pressure. An annular groove at the inner side of the end wall surrounds the bead and communicates with the atmosphere by way of at least one channel in the cylindrical portion. The groove communicates with the atmosphere during expulsion of air from the bottle, for example, in response to heating, but is sealed from the interior of the bottle when the end wall bulges inwardly and maintains the bead in sealing engagement with the neck. A suspending device for the cap has a yoke-like section whose ends are secured to the cylindrical portion of the cap and which is articulately connected with a hooked second section enabling a nurse to attach the bottle to a hospital bed. The first section has a slit which can receive and thereby seals a portion of the hose. The free end of the hose is connectable to a conduit which is inserted into or placed next to a wound to collect pus or other excretion.

10 Claims, 3 Drawing Figures

CLOSURE FOR VACUUM BOTTLES AND THE LIKE

BACKGROUND OF THE INVENTION

The present invention relates to improvements in containers in general, and more particularly to improvements in closures or caps for glass bottles, plastic bottles or analogous containers. Still more particularly, the invention relates to improvements in bottles or analogous containers which can be used for evacuation of pus or other liquid matter from animal bodies with the assistance from other-than-atmospheric pressure.

It is known to utilize vacuum-sealed liquid collection bottles in hospitals and similar institutions. The closure of the bottle is connected with a conduit which is placed adjacent to or into a wound to draw pus from the infected area and to thus promote the healing process. The liquid matter is caused to flow into one end of the conduit by evacuating air from the bottle whose closure is in communication with the other end of the conduit. As a rule, the conduit is discarded after a single use.

In certain presently known liquid collection bottles, the closure consists of a rubber disk which is overlapped by a nut made of synthetic plastic material and having internal threads in mesh with external threads on the neck portion of the bottle. The nut biases the disk against the end face of the neck portion so that the deformed disk establishes an airtight seal between the interior and exterior of the bottle. The means for indicating the presence and/or the extent of vacuum in the bottle forms an integral part of the disk. To this end, the latter is provided with two notches or recesses bounded at their outer ends by relatively thin elastic portions which constitute membranes and undergo deformation when the pressure at the outer side of the disk exceeds the pressure in the interior of the bottle. The membranes carry outwardly extending flags which are retracted into the disk when the pressure in the interior of the bottle is less than atmospheric pressure. Moreover, the flags move away from each other in response to deformation of the respective membranes so that, by observing the angle between the flags, a person can discern the presence as well as the extent of subatmospheric pressure in the interior of the bottle. A skilled nurse or another attendant in a hospital can determine whether or not the pressure in the bottle is sufficiently low to warrant the attachment of a conduit which is to evacuate liquid matter from wounds.

The recesses in the elastic disk are actually relatively deep blind bores. This presents problems when the apparatus must be cleaned and sterilized prior to renewed use, i.e., the cleaning of surfaces surrounding the deep blind bores is a time-consuming task and the person in charge is not absolutely sure whether or not such surfaces are sufficiently clean for renewed use of the disk. Furthermore, threading of the nut onto and detachment of the nut from the neck portion of the bottle is a time-consuming procedure.

U.S. Pat. No. 3,334,628 to Saemann et al. discloses a vacuum indicating connection for surgical wound-closing apparatus wherein the open end of the neck portion of a bottle is closed by an internally threaded cap and the open end is sealed by a rubber membrane which is overlapped by the cap and is pressed against the end face of the neck portion. The membrane is connected with a hose passing through a central opening of the end wall of the cap. When the pressure in the bottle is reduced below atmospheric pressure, the membrane bulges inwardly and pulls the adjacent end portion of the hose through the opening of the cap and into the neck portion of the bottle. Since the membrane is not observable from without, the patented device comprises a rather complex indicating system which can be observed by an attendant in order to determine the extent of subatmospheric pressure in the bottle. Such system includes a sleeve which extends outwardly from the end wall of the cap and has a window in line with different indicia on the hose. As the hose moves axially in response to deformation of the membrane, it places different indicia into register with the window which can be observed from without. The complexity of the indicating system contributes to initial cost and the sterilizing operation must be preceded by a time-consuming dismantling of the apparatus.

OBJECTS AND SUMMARY OF THE INVENTION

An object of the invention is to provide a novel and improved closure for the neck portion of a glass bottle or an analogous container, especially a closure for bottles which can be used in hospitals and wherein the pressure differs from the pressure of the surrounding atmosphere when the containers are in use.

Another object of the invention is to provide an assembly of a bottle and a closure which latter is simpler than heretofore known closures and is constructed and configurated in such a way that the assembly can be taken apart and reassembled with little loss in time whereby the components of the assembly can be readily and reliably cleaned and sterilized upon detachment of the closure, and which can furnish readily discernible indications of the pressure differential between the interior and exterior of the bottle.

A further object of the invention is to provide a simple device which enables an attendant to rapidly detach the closure from the container as well as to suspend the assembly at a convenient location, e.g., on a selected portion of a bed.

An additional object of the invention is to provide a self-sealing closure for use in the above outlined assembly.

An ancillary object of the invention is to provide a closure which can be used with many existing types of bottles or analogous containers.

The invention is embodied in a combination which includes a container having an open-ended neck portion and an elastic closure or cap including a substantially cylindrical portion surrounding the neck portion of the container and an end wall integral with one end of the cylindrical portion and extending across the open end of the neck portion. The end wall is readily deformable in response to establishment of a pressure differential between the interior and exterior of the container whereby the extent of deformation of the end wall furnishes a visually detectable indication of the magnitude of the pressure differential. The end wall has a preferably centrally located opening and is connected with a conduit, preferably a flexible hose, which communicates with the interior of the container via opening in the end wall.

The outer side of the end wall is preferably provided with at least one projection (e.g., a diametrically extending rib) which is movable in response to deformation of the end wall to thus facilitate determination of the extent of such deformation.

The novel features which are considered as characteristic of the invention are set forth in particular in the appended claims. The improved assembly itself, however, both as to its construction and the mode of assembling or dismantling the same, together with additional features and advantages thereof, will be best understood upon perusal of the following detailed description of certain presently preferred embodiments with reference to the accompanying drawing.

DESCRIPTION OF THE PREFERRED EMBODIMENTS

Figure 1:
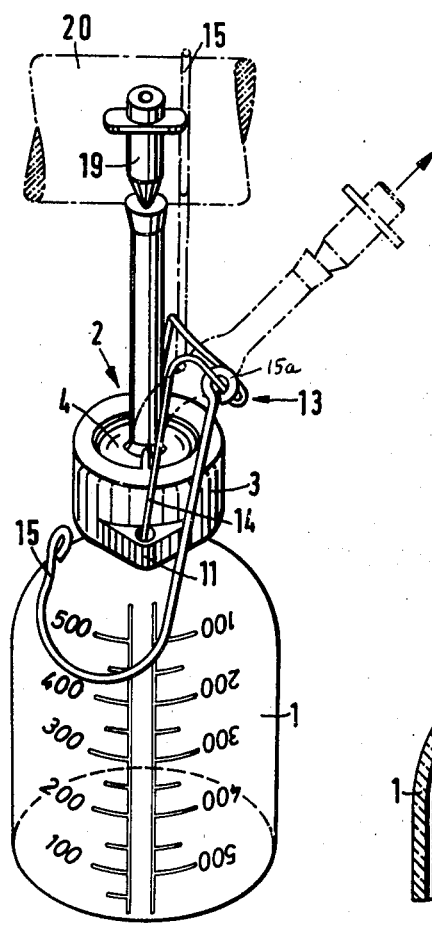
FIG. 1 is a perspective view of an assembly including a glass bottle and a closure therefor which embodies one form of the invention.
Figure 2:
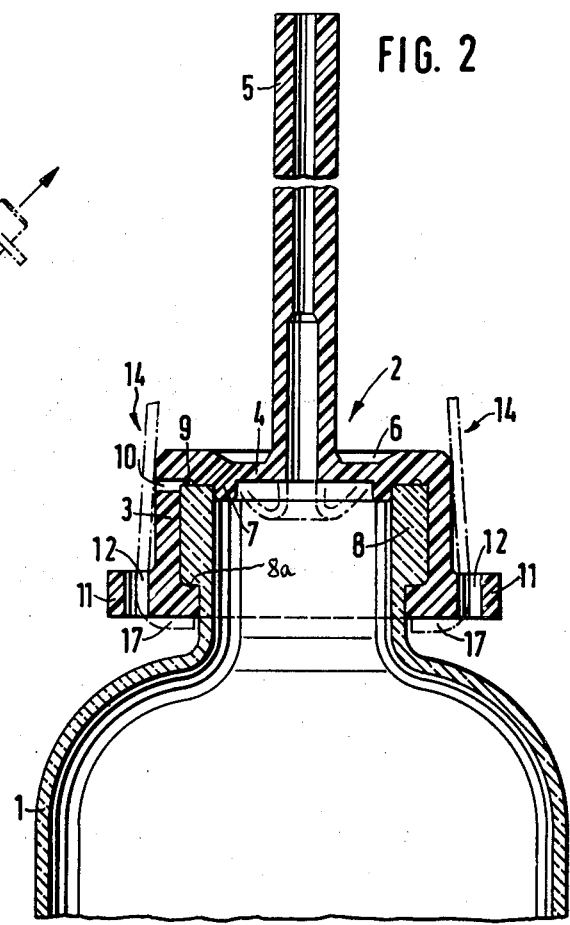
FIG. 2 is an enlarged fragmentary axial sectional view of the bottle and an axial sectional view of the closure.

FIGS. 1 and 2 show a container or bottle 1 having a neck portion 8 which is connected with an elastic closure or cap 2 consisting of rubber or the like. The cap 2 comprises a substantially cylindrical portion 3 which surrounds the neck portion 8 of the bottle 1 and has a lower end provided with an inwardly extending collar overlying an external shoulder 8a of the neck portion. The upper or outer end of the cylindrical portion 3 is integral with a transversely extending portion or end wall 4 which overlies the open end of the neck portion 8 and constitutes a deformable membrane. Thus, when the pressure at the outer side of the end wall 4 exceeds the pressure in the interior of the bottle, the end wall 4 is deformed, i.e., it bulges inwardly to the extent which is indicative of the pressure differential between the inner and outer sides thereof. One of several deformed conditions of the end wall 4 is indicated in FIG. 2 by phantom lines.

The median portion of the end wall 4 is integral with a flexible conduit or hose 5 whose open end can be coupled to a drainage conduit which is inserted into a wound and serves for evacuation of liquid matter. The central part of the end wall 4 is formed with an opening which establishes communication between the interior of the bottle 1 and the hose 5. The outer side of the end wall 4 is further formed with at least one diametrically extending projection or rib 6 whose primary purpose is to facilitate visual determination of the extent of deformation of the end wall in response to evacuation of air from the interior of the bottle 1. The rib 6 and its movements can be readily observed from the exterior of the cap 2.

The inner side of the end wall 4 has an annular protuberance or bead 7 which is closely adjacent to the inner surface of the neck portion 8 and sealingly engages such inner surface in response to deformation of the end wall 4, i.e., in response to evacuation of air from the interior of the bottle 1. An annular groove 9 which surrounds the protuberance 7 and is provided in the inner side of the end wall 4 communicates with at least one radially outwardly extending air-evacuating channel 10 which is formed in the cylindrical portion 3 of the cap 2. The expulsion of air from the interior of the bottle 1 can be carried out as follows: The hose 5 is sealed and the bottle 1 is heated so that air which is confined therein expands and escapes by flowing along the path defined by the passage including the groove 9 and channel or channels 10. The bottle 1 is thereupon cooled whereby the remnant of entrapped air therein contracts and the pressure in the bottle drops below the pressure of the surrounding atmosphere. The external pressure acts upon the outer side of the end wall 4 which is deformed (e.g., to the extent indicated in FIG. 2 by phantom lines) whereby the outer diameter of the protuberance increases and the protuberance establishes a reliable seal between the cap 2 and the inner surface of the neck portion 8.

The groove 9 and channel or channels 10 can be omitted if the free end portion of the hose 5 contains a removable check valve 19 (shown in FIG. 1) which allows air to escape from the interior of the bottle during heating but prevents inflow of air during cooling of the bottle.

Figure 3:
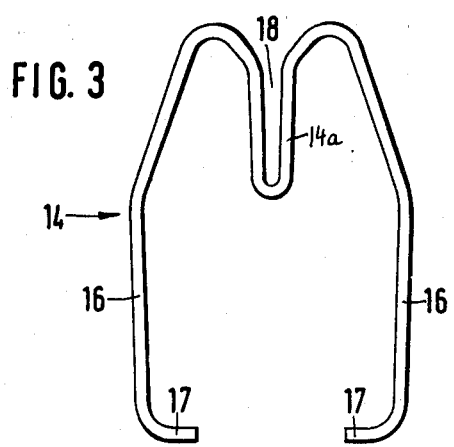
FIG. 3 is an elevational view of one section of a suspending device for the closure.

That end of the cylindrical portion 3 of the cap 2 which is remote from the end wall 4 further comprises two outwardly extending projections or lugs 11 which are but need not be located diametrically opposite each other and have holes 12 for the legs 16 of a yoke-like section 14 of a suspending device 13. The latter further comprises a substantially hook-shaped second section 15 which can be used to suspend the bottle 1 on a part 20 of a bed in a hospital or a similar institution. The legs 16 of the section 14 have inwardly extending bent-over ends 17 (see also FIG. 3) which are located below the respective holes 12 and overlie the lower end of the cylindrical portion 3 to insure that the section 14 is coupled to the cap 2. The upper portion of the section 14 is looped, as at 14a, to define a narrow slit 18 which is open at one end and can receive a portion of the hose 5. The slit is sufficiently narrow to insure that the looped portion 14a seals that part of the hose 5 which is inserted into the slit so that the outer end of the hose is then sealed from the interior of the bottle 1.

The material of the section 14 is preferably at least slightly elastic (this section may consist of steel wire) and the ends 17 can serve the additional purpose of facilitating detachment of the cap 2 from the neck portion 8. All a person wishing to evacuate the contents of the bottle 1 and to thereupon sterilize the parts 1, 2 and 5 has to do is to pull the section 14 in a direction to detach the cap from the neck portion 8. Such separation of the cap 2 will normally take place when the pressure differential between the inner and outer sides of the end wall 4 is relatively small so that the pressure differential does not offer a pronounced resistance to detachment of the cap.

When the intermediate portion of the hose 5 is received in and deformed by the looped portion 14a of the section 14, the check valve 19 at the upper end of the hose can be removed and the hose is then connected with the aforementioned drainage conduit (not shown) serving for evacuation of liquid matter from a wound. The hose 5 is thereupon withdrawn from the slit 18 so that the drainage conduit is in communication with the interior of the bottle 1.

The upper section 15 of the suspending device 13 has an eyelet 15a which slidably surrounds a portion of the section 14. As mentioned above, the major part of the section 15 is hooked so that it can be readily attached to a hospital bed (part 20 in FIG. 1) in an optimum position to insure the flow of liquid matter from a wound or abscess into the bottle 1.

The cap 2 can be designed in such a way that the annular protuberance 7 moves away from the inner surface of the neck portion 8 when the pressure of the surrounding air (and hence the pressure in the passage including the channel or channels 10 and groove 9) exceeds a predetermined pressure (e.g., 1.2 atmospheres superatmospheric pressure). If the groove 9 and channel or channels 10 are omitted, the check valve 19 is designed in such a way that it allows air to flow into the bottle 1 when the pressure of the surrounding atmosphere exceeds a preselected value and the valve allows air to flow from the interior of the bottle below such predetermined pressure. The exact construction of the check valve 19 forms no part of the invention; this element may constitute a commercially available mass-produced article.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalance of the appended claims.

What is claimed is:

1. The combination of a container including a neck portion having an open end and an inner surface with a detachable elastic closure comprising a substantially cylindrical portion surrounding said neck portion and having a first and a second end, and an end wall integral with said first end and extending across said open end, said end wall having a substantially centrally located opening and being readily deformable in response to establishment of a pressure differential between the interior and exterior of said contaner whereby the extent of deformation of said end wall furnishes a visually detectable indication of said pressure differential, a conduit comprising a flexible hose sealingly connected with said end wall and communicating with the interior of said container via said opening, and a suspending device for said closure, said suspending device comprising a section having two legs connected to said cylindrical portion and a further portion defining a slit, said hose being insertable into said slit and the width of said slit being such that said further portion deforms and seals said hose when the latter is inserted into said slit.

2. The combination of claim 1, wherein said end wall has an inner side and an outer side and comprises at least one projection at said outer side thereof, said projection being movable in response to deformation of said end wall to thus facilitate determination of the extent of such deformation.

3. The combination of claim 2, wherein said projection is a rib extending substantially diametrically of said end wall.

4. The combination of claim 1, wherein said closure has at least one passage which establishes a path for the flow of air between the interior and exterior of said container in undeformed condition of said end wall.

5. The combination as defined in claim 4, wherein said end wall has an inner side and an outer side and said passage includes an annular groove in said inner side and at least one channel connecting said groove with the surrounding atmosphere.

6. The combination of claim 1, wherein said end wall comprises an annular protuberance which sealingly engages the inner surface of said neck portion in response to a reduction of pressure at said inner side below the pressure at the exterior of said container.

7. The combination of claim 1, wherein said legs are located at the diametrically opposite sides of said neck portion.

8. The combination of claim 1, wherein said legs have bent-over ends overlying the second end of said cylindrical portion.

9. The combination of claim 1, wherein said suspending device further comprises a substantially hook-shaped second section articulately coupled to said first mentioned section.

10. The combination of claim 9, wherein said second section has an eyelet slidably surrounding a part of said first mentioned section.

* * * * *